United States Patent
Eppstein

(10) Patent No.: US 6,183,434 B1
(45) Date of Patent: Feb. 6, 2001

(54) MULTIPLE MECHANICAL MICROPORATION OF SKIN OR MUCOSA

(75) Inventor: Jonathan A. Eppstein, Atlanta, GA (US)

(73) Assignees: SpectRx, Inc., Norcross, GA (US); Altea Technologies, Inc., Atlanta, GA (US)

(*) Notice: Under 35 U.S.C. 154(b), the term of this patent shall be extended for 0 days.

(21) Appl. No.: 09/202,207

(22) PCT Filed: Jul. 3, 1997

(86) PCT No.: PCT/US97/11670

§ 371 Date: Jun. 14, 1999

§ 102(e) Date: Jun. 14, 1999

(87) PCT Pub. No.: WO98/00193

PCT Pub. Date: Jan. 8, 1998

Related U.S. Application Data

(60) Provisional application No. 60/021,212, filed on Jul. 3, 1996.

(51) Int. Cl.⁷ ..................................................... A61B 17/20
(52) U.S. Cl. ........................... 604/22; 424/449; 606/186; 600/362; 600/583
(58) Field of Search ............................... 604/20–21, 501, 604/22; 606/186; 424/449; 600/362, 573, 578, 583

(56) References Cited

U.S. PATENT DOCUMENTS

| | | |
|---|---|---|
| 3,964,482 | 6/1976 | Gerstel et al. . |
| 4,340,048 * | 7/1982 | Eckenhoff . |
| 4,522,622 | 6/1985 | Perry et al. . |
| 4,775,361 * | 10/1988 | Jacques et al. . |
| 5,115,805 | 5/1992 | Bommannan et al. . |
| 5,137,817 * | 8/1992 | Busta et al. . |
| 5,169,389 | 12/1992 | Kriesel . |
| 5,223,219 | 6/1993 | Subramanian et al. . |
| 5,250,023 | 10/1993 | Lee et al. . |
| 5,279,544 | 1/1994 | Gross et al. . |
| 5,421,816 | 6/1995 | Lipkovker . |
| 5,445,611 * | 8/1995 | Eppstein et al. . |
| 5,458,140 * | 10/1995 | Eppstein et al. . |
| 5,801,057 | 9/1998 | Smart et al. . |
| 5,882,317 * | 3/1999 | Saito et al. . |
| 6,022,316 * | 3/1999 | Godshall et al. . |
| 6,027,459 | 2/2000 | Shain et al. . |

FOREIGN PATENT DOCUMENTS

| | | |
|---|---|---|
| 0 497 620 A2 | 5/1992 | (EP) . |
| 2 221 394 | 7/1990 | (GB) . |
| 95/10223 * | 4/1995 | (WO) . |
| WO 96/17648 | 6/1996 | (WO) . |
| 97/07734 * | 3/1997 | (WO) . |
| WO 98/24366 | 6/1998 | (WO) . |
| 98/291134 * | 7/1998 | (WO) . |
| WO 99/27852 | 6/1999 | (WO) . |
| WO 99/40848 | 8/1999 | (WO) . |

* cited by examiner

Primary Examiner—Mark Bockleman
(74) Attorney, Agent, or Firm—Needle & Rosenberg

(57) ABSTRACT

A method of enhancing the permeability of a biological membrane, including the skin or mucosa of an animal or the outer layer of a plant to a permeant is described utilizing microporation of selected depth and optionally one or more of sonic, electromagnetic, mechanical and thermal energy and a chemical enhancer. Microporation is accomplished to form a micropore of selected depth in the biological membrane and the porated site is contacted with the permeant. Additional permeation enhancement measures may be applied to the site to enhance both the flux rate of the permeant into the organism through the micropores as well as into targeted tissues within the organism.

48 Claims, 5 Drawing Sheets

MULTIPLE MECHANICAL MICROPORATION OF SKIN OR MUCOSA

CROSS REFERENCE TO RELATED APPLICATIONS

This application is a 371 of PCT/US97/11670 which claims the benefit of U.S. Provisional Application Ser. No. 60/021,212, filed Jul. 3, 1996.

BACKGROUND OF THE INVENTION

This invention relates to a device and method for puncturing a selected layer or layers of the skin or mucosa. More particularly, the invention relates a device and method for puncturing the stratum corneum or mucosa to diminish the barrier function thereof and permit a drug to be delivered to the body or an analyte in the body to be withdrawn for monitoring. This puncturing of the stratum corneum or mucosa is minimally invasive, and can be combined with various other methods, such as use of chemical enhancers, pressure gradients, sonic gradients, temperature gradients, and the like for selectively enhancing the inward flux of a drug to the body or the outward flux of an analyte from the body.

The stratum corneum is chiefly responsible for the well-known barrier properties of skin. Thus, it is this layer of the skin that presents the greatest barrier to transdermal flux of drugs or other molecules into the body and of analytes out of the body. Mucosal tissue also presents a barrier to flux of molecules into and out of the body. The stratum corneum, the outer horny layer of the skin, is a complex structure of compact keratinized cell remnants separated by lipid domains. Compared to the oral or gastric mucosa, the stratum corneum is much less permeable to molecules either external or internal to the body. The stratum corneum is formed from keratinocytes, which comprise the majority of the epidermal cells, that lose their nuclei and become corneocytes. These dead cells comprise the stratum corneum, which has a thickness of about 10–30 $\mu$m and, as noted above, is a very resistant waterproof membrane that protects the body from invasion by exterior substances and the outward migration of fluids and dissolved molecules. The stratum corneum is continuously renewed by shedding of corneum cells during desquamation and the formation of new corneum cells by the keratinization process.

Various methods of enhancing the permeability of the stratum corneum and mucosa have been described. For example, U.S. Pat. No. 5,458,140 and U.S. Pat. No. 5,445,611 disclose using ultrasonic energy that is modulated in intensity, phase, or frequency or a combination thereof. U.S. Pat. No. 4,775,361 discloses a method of administering a drug by ablating the stratum corneum using pulsed laser light without significantly damaging the underlying epidermis. Numerous patents teach the use of chemical enhancers for improving transdermal flux of a drug through the skin. E.g, U.S. Pat. No. 4,863,970. It would be advantageous to develop additional methods of permeating the stratum corneum or mucosa to enhance the transport of drugs into the body or analytes out of the body, particularly without the need for expensive or complicated equipment.

In view of the foregoing, it will be appreciated that providing a device and method of use thereof for introducing multiple micropores or perforations in the stratum corneum or mucosa for enhancing transport of molecules therethrough would be a significant advancement in the art.

BRIEF SUMMARY OF THE INVENTION

It is an object of the present invention to provide a simple, inexpensive device for puncturing the stratum corneum or mucosa without significantly damaging the underlying tissues to facilitate transport of molecules therethrough.

It is also an object of the invention to provide a method of enhancing the passage of molecules through the stratum corneum or mucosa.

It is another object of the invention to provide a method for transdermally or transmucosally delivering a drug.

It is still another object of the invention to provide a method for transdermally or transmucosally monitoring an analyte.

These and other objects can be achieved by providing a device for reducing the barrier properties of skin or mucosa to the delivery of a substance into the body or the withdrawal of an analyte from the body comprising:

(a) a base having a lower side and an upper side;

(b) a plurality of puncturing members extending from the lower side of the base, the puncturing members configured for puncturing the skin or mucosa to a depth sufficient to reduce the barrier properties thereof without significantly damaging underlying tissues;

(c) a plurality of holes extending from the lower side of the base to the upper side of the base, the holes configured for permitting a liquid to move therethrough by capillary action; and (d) a network of channels configured in the upper side of the base to interconnect the holes.

Preferably, the device is fabricated by microlithography and is composed of a material selected from the group consisting of silicon, metal, and plastic. It is also preferred that the puncturing member be in the shape of a pyramid or wedge. The pyramid or wedge preferably have sharp edges having corner radii of less than 1 $\mu$m. The puncturing member is preferably configured for puncturing the skin or mucosa to a depth of about 30–50 $\mu$m, and a dimension at a base thereof is preferably about 10–50 $\mu$m. The puncturing members preferably occupy up to about 50% of the surface area of the lower surface of the base.

The device preferably further comprises a mechanism for producing vibrations, the vibrations for facilitating efficient and non-traumatic penetration of the puncturing members into the skin or mucosa. A preferred vibration-producing mechanism comprises a piezo-electric transducer. It is preferred that the mechanism for producing vibrations produces vibrations in the range of about 2000 Hz to about 100 MHz.

In another illustrative embodiment of the device, an external reservoir for holding a liquid drug composition to be delivered to the body is provided. Still further, a mechanism for limiting the rate of drug delivery is preferably included in the device, the mechanism positioned between the external reservoir and the puncturing members. Such rate-limiting mechanisms can include selective permeability membranes and valve mechanisms. In another preferred embodiment, the device is disposable.

A method for reducing the barrier function of skin or mucosa to the delivery of substances into a body or withdrawal of analytes out of the body, comprises:

(a) providing a device comprising:
   a base having a lower side and an upper side;
   a plurality of puncturing members extending from the lower side of the base, the puncturing members configured for puncturing the skin or mucosa to a depth sufficient to reduce the barrier properties thereof without significantly damaging underlying tissues;
   a plurality of holes extending from the lower side of the base to the upper side of the base, the holes configured for permitting a liquid to move therethrough by capillary action; and a network of channels configured in the upper side of the base to interconnect the holes;

(b) contacting the device with the skin or mucosa such that the plurality of puncturing members puncture the skin or mucosa to a depth sufficient to reduce the barrier properties thereof.

A method of transdermal or transmucosal monitoring of a selected analyte in a body comprises:

(a) providing a device comprising:

a base having a lower side and an upper side;

a plurality of puncturing members extending from the lower side of the base, the puncturing members configured for puncturing said skin or mucosa to a depth sufficient to reduce the barrier properties thereof without significantly damaging underlying tissues;

a plurality of holes extending from the lower side of the base to the upper side of the base, the holes configured for permitting a liquid to move therethrough by capillary action; and a network of channels configured in the upper side of the base to interconnect the holes, the network of channels including a reservoir;

(b) contacting the device with the skin or mucosa such that the plurality of puncturing members puncture the skin or mucosa to a depth sufficient to reduce the barrier properties thereof resulting in seepage of interstitial fluid to the surface of the skin or mucosa such that interstitial fluid moves by capillary action through the holes, through the channels, to the reservoir;

(c) collecting the interstitial fluid from the reservoir; and (d) analyzing the interstitial fluid with respect to the selected analyte.

In a preferred embodiment, the method further comprises applying suction to increase the rate of collection of interstitial fluid. Ultrasonic vibrations can also be applied to the skin or mucosa to increase the rate of collection of the selected analyte. The ultrasonic vibrations can be modulated in frequency, intensity, phase, or a combination thereof, as disclosed in U.S. Pat. No. 5,458,140, hereby incorporated by reference. The ultrasonic vibrations are preferably in the range of about 2000 Hz to about 100 MHz. The ultrasonic vibrations can also enhance the movement of interstitial fluid by capillary action. In a preferred embodiment of the invention, the selected analyte is glucose. It is also preferred to apply an anticoagulant to inhibit obstruction of the holes or channels.

A method of transdermally or transmucosally delivering a drug in liquid form to a body comprises:

(a) providing a device comprising:

a base having a lower side and an upper side;

a plurality of puncturing members extending from the lower side of the base, the puncturing members configured for puncturing the skin or mucosa to a depth sufficient to reduce the barrier properties thereof without significantly damaging underlying tissues;

a plurality of holes extending from the lower side of the base to the upper side of the base, the holes configured for permitting a liquid to move therethrough by capillary action; and a network of channels configured in the upper side of the base to interconnect the holes, the network of channels including a reservoir;

(b) contacting the device with the skin or mucosa such that the plurality of puncturing members puncture the skin or mucosa to a depth sufficient to reduce the barrier properties thereof;

(c) supplying the drug to the reservoir such that said drug moves from the reservoir, through the channels and holes to the site of the punctures of the skin or mucosa and thus into the body.

In a preferred embodiment, pressure is applied to increase the rate of delivery of the drug to the body. Applying ultrasonic vibrations to the skin or mucosa also increases the rate of delivery of the drug to the body. The ultrasonic vibrations can be modulated in frequency, intensity, phase, or a combination thereof, as disclosed in U.S. Pat. No. 5,445,611, hereby incorporated by reference. The ultrasonic vibrations are preferably in the range of about 2000 Hz to about 100 MHz. The drug in liquid form can further comprise an anti-irritant, antiseptic, or analgesic to reduce trauma to the body due to the application of the device.

DETAILED DESCRIPTION

Figure 1:
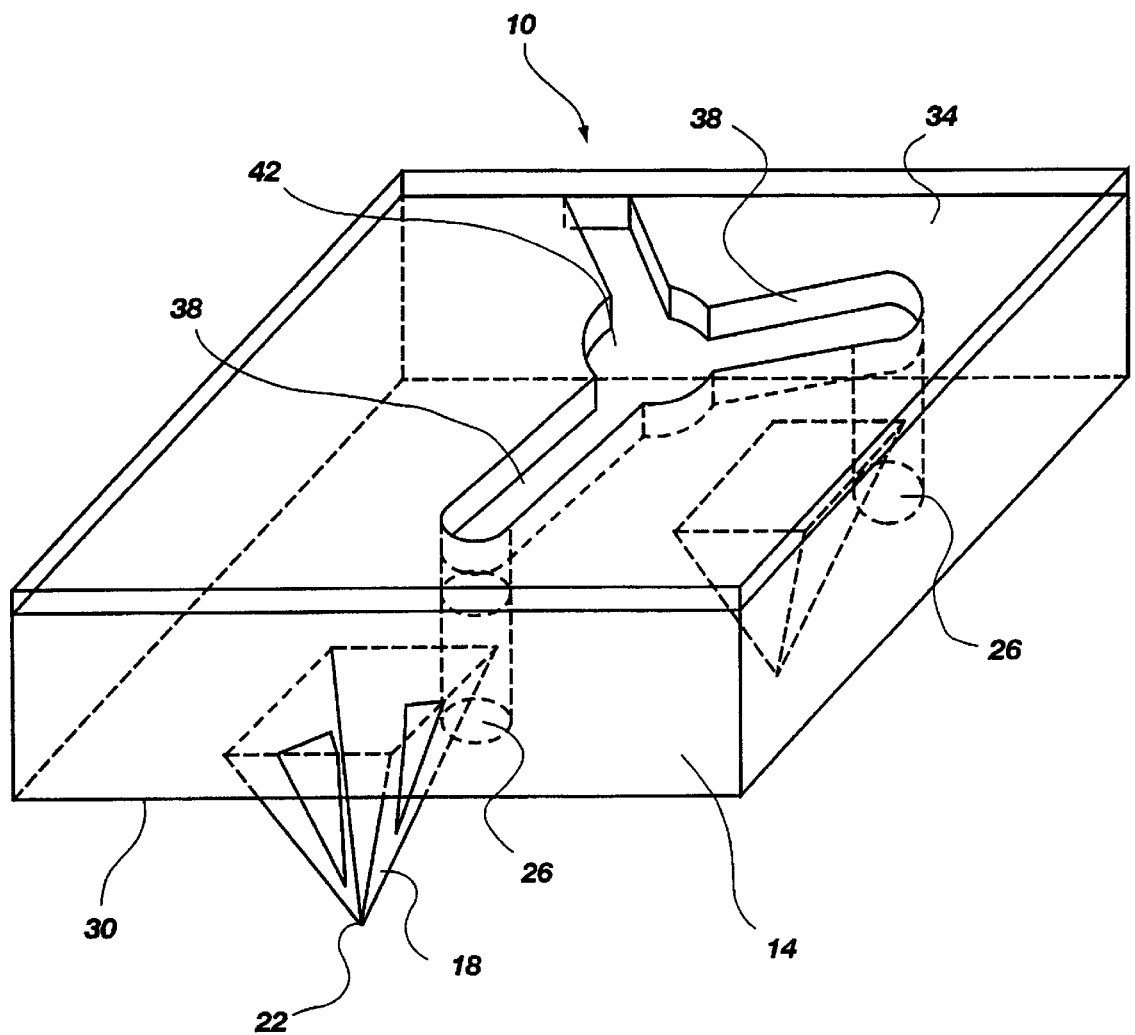
FIG. 1 shows a perspective view of an illustrative embodiment of the present invention.

Before the present device and method for enhancing permeability of skin or mucosa for drug delivery or analyte monitoring are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a device containing "a puncturing member" includes a device containing two or more of such members, reference to "a channel" includes reference to one or more of such channels, and reference to "an ultrasound transducer" includes reference to two or more ultrasound transducers.

It has been observed that forming a hole or micropore, 30 µm across, in the stratum corneum yields a quick source of about 0.2 microliters of interstitial fluid seeping through the hole from the underlying tissue without any additional pumping. Merely increasing the number of holes introduced through the stratum corneum would increases the amount of passively available fluid in a linear fashion. That is, creating 100 holes should produce about 20 microliters of interstitial fluid. From a practical perspective, using known approaches to create 100 holes in a controlled pattern would be challenging and time-consuming. However, using the mechanical puncturing capabilities of a mechanical microporation or "bed-of-nails" device would allow an almost unlimited number of micropores to be quickly created in any selected pattern. Similarly, using conventional lancet and needle technologies would make the needed depth control of the puncture very tricky and, if the device were to create hundreds of these holes, the mechanical challenge of building the device using conventional metal needle technologies would be formidable. However, by fabricating puncturing elements en masse such that they protrude from a substantially planar surface, with sufficient spacing between each to allow the stratum corneum to come in contact with this intervening planar surface, the absolute length of the puncturing elements themselves would act as an accurate limit for the depth of the micropore. Also, using a microlithography approach to fabricate these structures will allow an entire surface comprised of puncturing elements and the interconnecting fluid management system to be built very cost effectively.

One illustrative method would be to utilize the existing base of manufacturing capabilities developed in the semiconductor and micro-mechanical industries to dry-etch an entire 4 inch silicon wafer with a network of these devices. This master could then be used as the basis for an electroplated mold from which thousands of copies could be produced. For a typical useable surface area/per device application of 4 mm×4 mm, one 4-inch wafer would yield more than 500 of the devices.

A device according to the present invention is made, for example, by first preparing a master by a dry etch process on a silicon wafer, as is well known in the art. Photolithographical processes for etching micrometer-scale structures into silicon waters and the like are described in A. T. Wooley & R. A. Mathies, Ultra-high-speed DNA fragment separations using microfabricated capillary array electrophoresis chips, 91 Biophysics 11348–52 (1994); C. S. Effenhauser et al., High-speed separation of antisense oligonucleotides on a micromachined capillary electrophoresis device, 66 Anal. Chem. 2949 (1994); C. Effenhauser et al., 65 Anal. Chem. 2637 (1993); Z. H. Fan & D. J. Harrison, Micromachining of capillary electrophoresis injectors and separators on glass chips and evaluation of flow at capillary intersections, 66 Anal. Chem. 177–84 (1994); W. H. Ko et al., in Sensors: A Comprehensive Survey, T. Grandke, W. H. Ko, eds., VCH Press: Weinheim, Germany, Vol. 1, pp. 107–68 (1989); K. E. Petersen, 70 Proc. IEEE 420–57 (1982), which are hereby incorporated by reference. The master silicon wafer is then used to make an electroplated mold, and then the mold is used to make copies of the device, all by processes well known in the art.

Also, by coupling the entire device to an ultrasonic transducer, several known advantages can be realized simultaneously. For example, ultrasound has been shown to enhance the smooth cutting ability of scalpels and other surgical devices and can be expected to facilitate the easy, painless penetration of the puncturing elements into the stratum corneum with very little pressure. The edges of the pyramidally shaped puncturing elements shown in FIG. 1 can easily be fabricated such that the corner radius is less than 10 nanometers, a sharpness similar to a surgical scalpel. Second, ultrasound has also been shown to greatly enhance capillary action, thus the amount of fluid that could be collected in a device containing a capillary collection system could be expected to be significantly greater than that provided by mere passive means. Third, by using the entire body of the puncturing elements to provide a conduit for the ultrasonic energy, a simple method is presented wherein the sonic energy is placed within the body where it can provide a positive pressure, and streaming action on the interstitial fluid from within the body outward towards a collection system of capillary channels coupling all fluid harvested into a central reservoir.

FIG. 1 shows a perspective view of an illustrative device according to the present invention. The device 10 comprises a base 14 with a plurality of puncturing members 18 extending therefrom. In a preferred embodiment, the base is substantially planar. Each puncturing member comprises a sharp point 22 or edge for puncturing the stratum corneum or mucosa. Since the stratum corneum can be up to about 30 $\mu$m thick, it is preferred that the puncturing element have a height of about 40–50 $\mu$m to ensure that the stratum corneum will be fully breached without significantly damaging the underlying tissue. A pyramid or wedge shape is a preferred shape for the puncturing member because of the ease with which such a shape can be formed by microfabrication techniques such as microlithography. In an illustrative puncturing element having a pyramid shape, the base of the pyramid would preferably have a square base about 30–40 $\mu$m on a side.

It is also preferred that the base have a plurality of holes 26 extending therethrough from the lower side 30, on which the puncturing element are disposed, to the upper side 34. Preferably, each puncturing element is adjacent to and paired with at least one hole for collecting the interstitial fluid that seeps out of the puncture in the stratum corneum. These holes should be dimensioned to permit the interstitial fluid to move by capillary action from the lower side of the device to the upper side, where the interstitial fluid can be collected. It is also preferred to interconnect the holes with capillary channels 38 that are formed in the upper side of the device. Preferably, such channels intersect at a reservoir 42. The interstitial fluid moves by capillarity from the micropore into the hole, through the channels, and to the reservoir, where the interstitial fluid is collected, such as with a micropipet. Additional fluid can be collected by applying suction to the microporated area of skin or mucosa.

Figure 2:
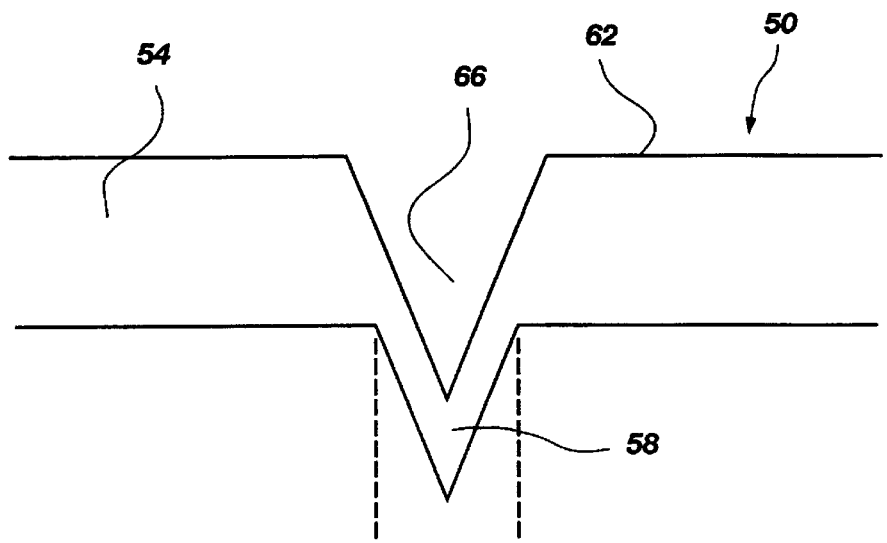
FIG. 2 shows a cross section of a portion of another illustrative embodiment according to the present invention.
Figure 3:
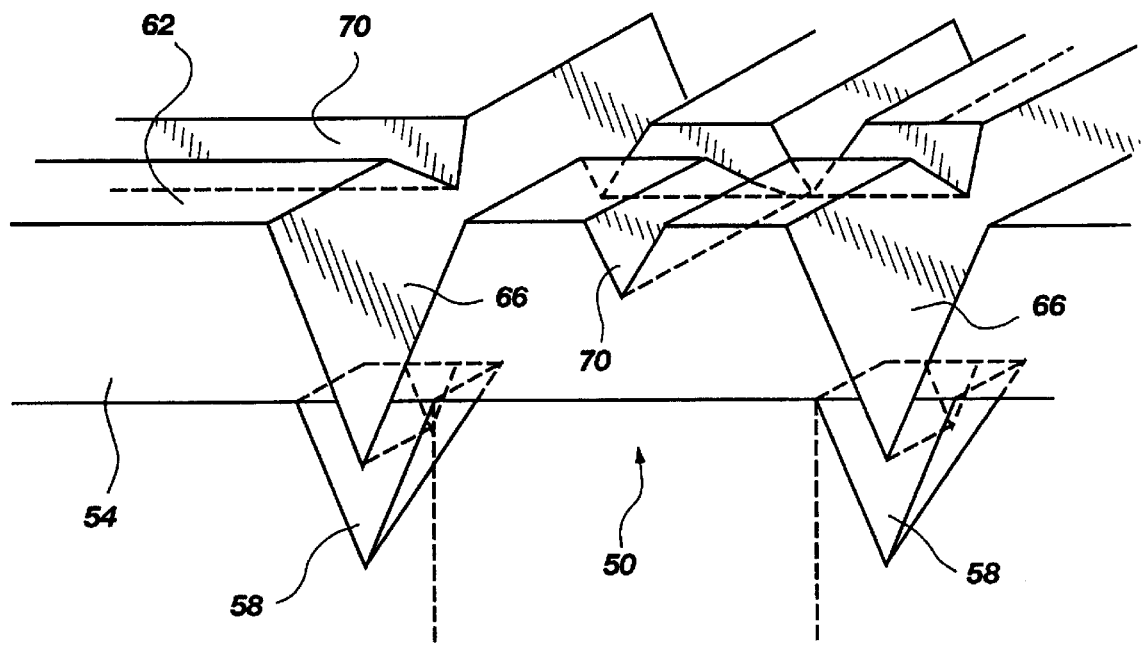
FIG. 3 shows a perspective view of a portion of the embodiment of FIG. 2.
Figure 4:
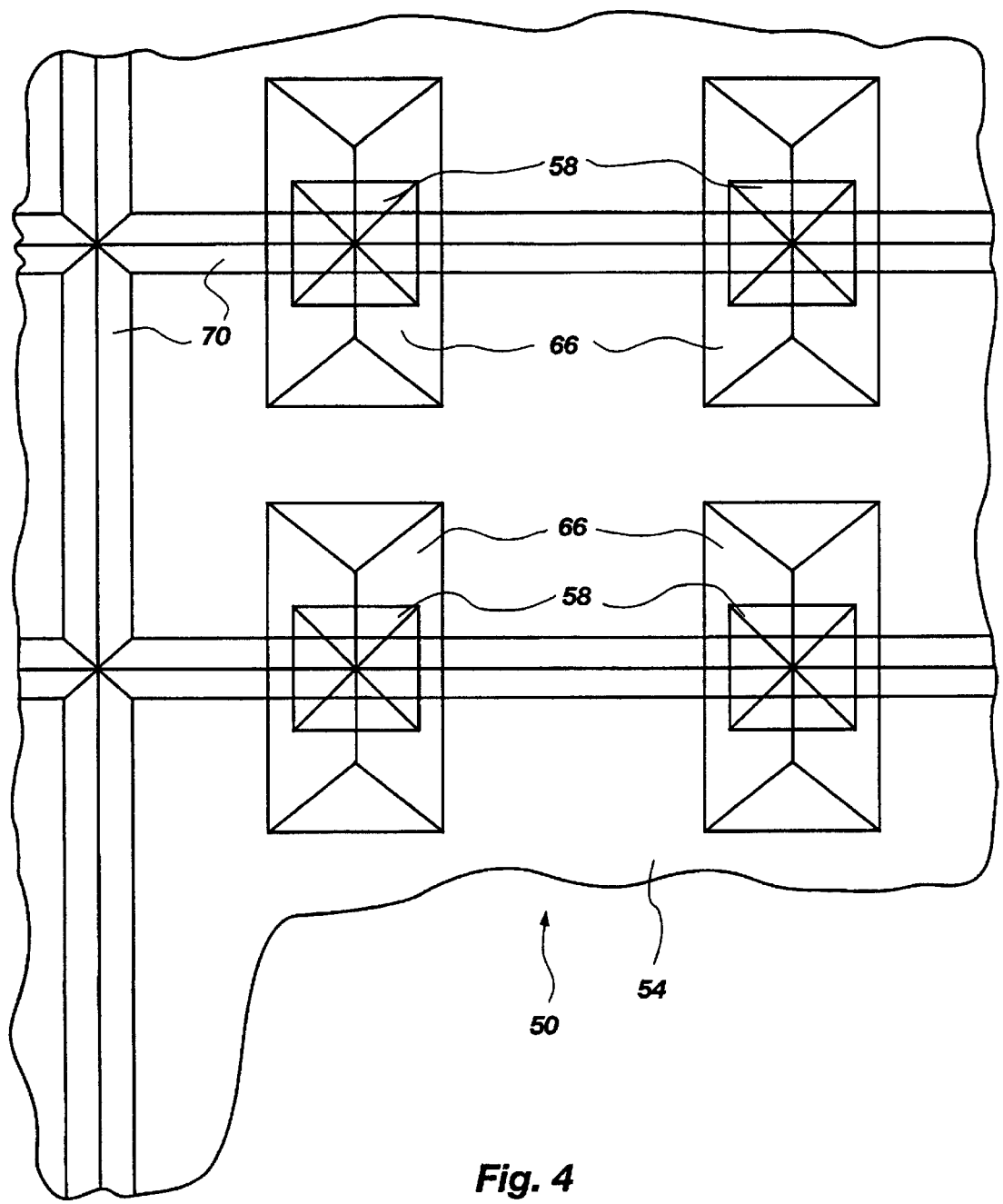
FIG. 4 shows a top view of a portion of the embodiment of FIG. 2.

FIGS. 2–4 show another illustrative embodiment of the invention. FIG. 2 shows a cross section of a portion of the device 50 comprising a base 54 with a puncturing member 58 extending therefrom. The puncturing member is pyramid-shaped, as in FIG. 1. The upper side 62 of the base is configured with a V-shaped channel 66 positioned such that the channel is directly over the puncturing member and cuts into the volume circumscribed by the puncturing member. FIG. 3 shows a perspective view of the device having the V-shaped channels 66 and interconnecting shallower V-grooves 70. The channels 66 cut through the lower side 74 of the base, and thus form openings through which the interstitial fluid can be taken up by capillary action. FIG. 4 shows how the V-grooves 70 interconnect the V-channels for collecting the interstitial fluid. All of the puncturing members, channels, and grooves shown in FIGS. 2,3, and 4 are designed to be wedge-shaped, compatible with being produced in the crystalline structure of a silicon substrate with a lithographic 'dry-etch' type of process.

Figure 5:
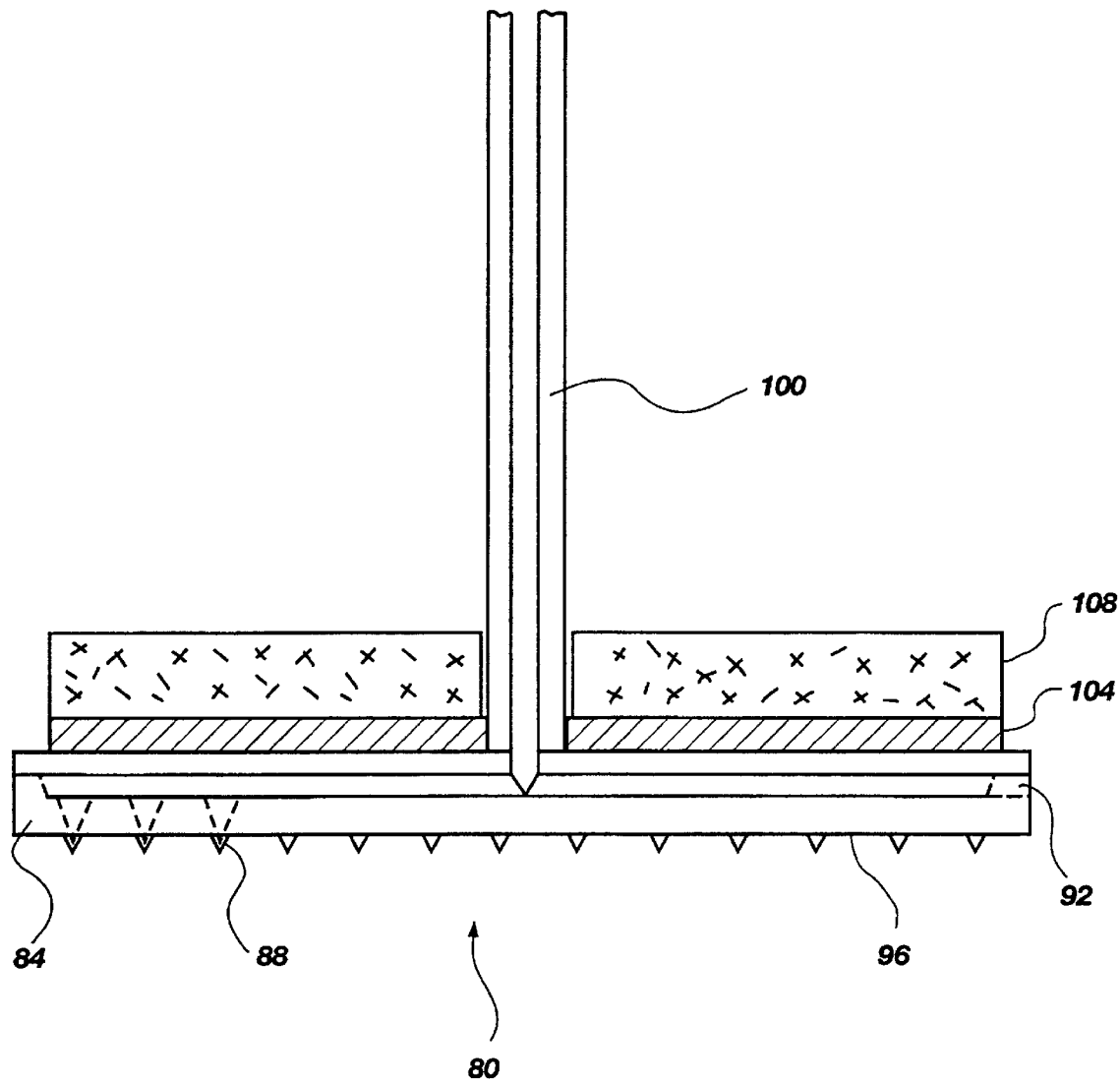
FIG. 5 shows a schematic diagram of a device for making multiple microporations in skin or mucosa and collecting interstitial fluid.

FIG. 5 shows an illustrative device 80 for collecting interstitial fluid according to the present invention. The device 80 comprises a base 84 having a plurality of puncturing members 88 extending therefrom. V-shaped channels and grooves are configured into the upper side 92 of the base for collecting the interstitial fluid. A cover plate 96 fits over the base to cover the network of channels and grooves and to inhibit evaporation of the interstitial fluid. The network of channels and grooves leads the interstitial fluid to a central area, where there is disposed a capillary tube 100 for receiving the interstitial fluid. Atop the cover plate is disposed an ultrasonic transducer 104 and a backing 108 for the tranducer.

The device is pressed against a selected area of skin or mucosa, and the ultrasonic transducer is activated to aid in both the puncturing of the tissue and in enhancing the seepage of the interstitial fluid. The interstitial fluid is collected by the network of openings in the base, and is conducted by the network of channels and grooves to the capillary, which takes up the fluid by capillary action. The fluid is then analyzed according to methods known in the art. An illustrative analyte is glucose, which can be quantified with various test strips that are available commercially.

Figure 6:
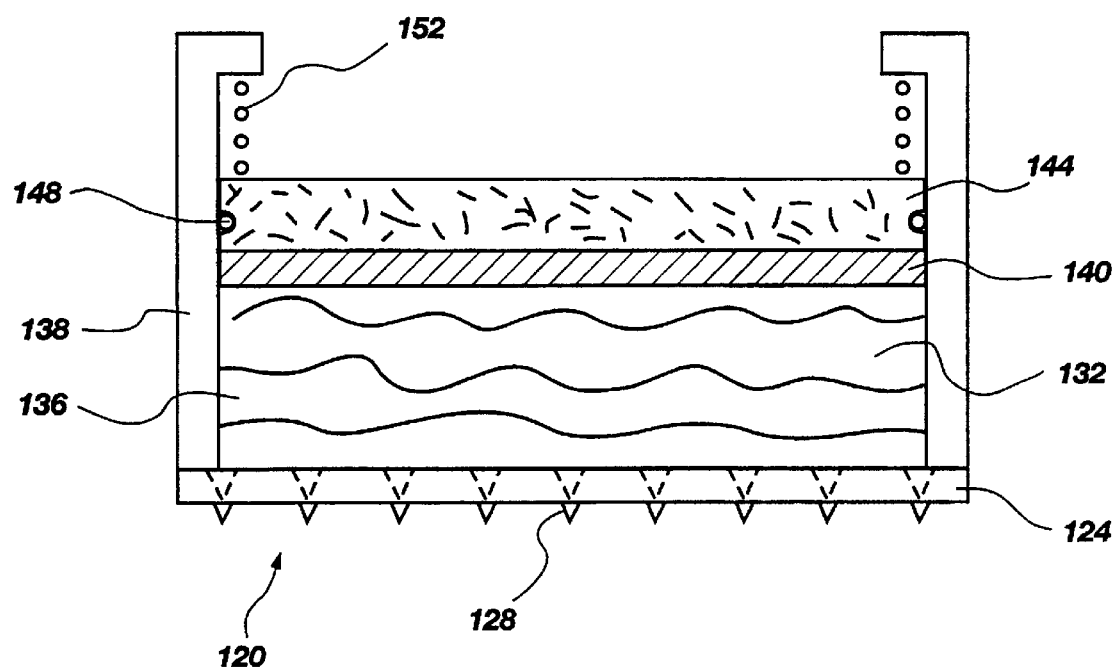
FIG. 6 shows a schematic sectional diagram of a device for making multiple microporations in skin or mucosa and delivering a drug.

FIG. 6 shows an illustrative drug delivery device 120 comprising a base 124 having a plurality of puncturing members 128 extending therefrom. A network of grooves and channels (see FIGS. 2–4) is embedded in the base for distributing a drug composition 132 from a reservoir 136. The reservoir is bounded by a housing 138, the base, and a backing plate 144 including an O-ring 148. The drug composition flows through the channels, grooves, and openings in the base to the surface of the skin or mucosa for entry into the body through the punctures or perforations. An ultrasound transducer 140 lies over the drug composition for aiding in delivery thereof. Above the transducer is the backing plate 144 including the O-ring for sealing the drug in the reservoir. A spring 152 can advantageously bias the backing plate against the transducer, which causes the transducer to be kept in fluid contact with the drug.

The ultrasonic system is utilized not only to enhance the slicing action of the edges of the puncturing elements as the penetrate into the stratum corneum or mucosa, but is then utilized to enhance the fluid flux of the therapeutic containing solution through the micro-pores and into the underlying tissues. In this case, large quantities of large molecular weight drugs could be delivered transdermally with a programmable control of the flux rate via variable activation of the ultrasonic pumping system. In addition, the sonic energy can be utilized to create controlled resonant vibrations in specifically shaped micro-structures such that a micro-pump is created to facilitate driving the collected fluid from one point to another within the entire structure. Moreover, chemical enhancers, air pressure, and other methods known in the art can be used to enhance the passage of the drug through the micropores in the skin or mucosa into the body.

I claim:

1. A device for reducing the barrier properties of skin or mucosa to the delivery of a substance into the body or the withdrawal of an analyte from the body comprising:
    (a) a base having a lower side and an upper side;
    (b) a plurality of puncturing members extending from the lower side of the base, said puncturing members configured for puncturing said skin or mucosa to a depth sufficient to reduce the barrier properties thereof without significantly damaging underlying tissues;
    (c) a plurality of holes extending from the lower side of the base to the upper side of the base, said holes configured for permitting a liquid to move therethrough by capillary action; and
    (d) a network of channels configured in the upper side of said base to interconnect said holes.

2. The device of claim 1 wherein said device is fabricated by microlithography.

3. The device of claim 1 wherein said device is fabricated of a material selected from the group consisting of silicon, metal, and plastic.

4. The device of claim 1 wherein said puncturing member is in the shape of a pyramid or wedge.

5. The device of claim 4 wherein said pyramid or wedge comprises sharp edges having corner radii of less than 1 $\mu$m.

6. The device of claim 1 wherein said puncturing member is configured for puncturing said skin or mucosa to a depth of about 30–50 $\mu$m.

7. The device of claim 1 wherein said plurality of puncturing members occupy up to about 50% of the surface area of the lower surface of the base.

8. The device of claim 1 wherein said puncturing member has a dimension at a base thereof of about 10–50 $\mu$m.

9. The device of claim 1 wherein said each of said holes is positioned adjacent to a puncturing member.

10. The device of claim 1 wherein said network of channels further comprises a reservoir for holding liquid.

11. The device of claim 1 wherein said base is substantially planar.

12. The device of claim 1 further comprising a mechanism for producing vibrations, said vibrations for facilitating efficient and non-traumatic penetration of the puncturing members into the skin or mucosa.

13. The device of claim 12 wherein said mechanism for producing vibrations comprises a piezo-electric transducer.

14. The device of claim 12 wherein said mechanism for producing vibrations produces vibrations in the range of about 2000 Hz to about 100 MHz.

15. The device of claim 1 further comprising an external reservoir for holding a liquid drug composition to be delivered to the body.

16. The device of claim 15 further comprising a mechanism for limiting the rate of drug delivery, said mechanism positioned between the external reservoir and the puncturing members.

17. The device of claim 1 wherein said device is disposable.

18. A method for reducing the barrier function of skin or mucosa to the delivery of substances into a body or withdrawal of analytes out of the body, comprising:
    (a) providing a device comprising:
        a base having a lower side and an upper side;
        a plurality of puncturing members extending from the lower side of the base, said puncturing members configured for puncturing said skin or mucosa to a depth sufficient to reduce the barrier properties thereof without significantly damaging underlying tissues;
        a plurality of holes extending from the lower side of the base to the upper side of the base, said holes configured for permitting a liquid to move therethrough by capillary action; and
        a network of channels configured in the upper side of said base to interconnect said holes;
    (b) contacting said device with the skin or mucosa such that said plurality of puncturing members puncture the skin or mucosa to a depth sufficient to reduce the barrier properties thereof.

19. The method of claim 18 wherein said device is fabricated by microlithography.

20. The method of claim 18 wherein said device is fabricated of a material selected from the group consisting of silicon, metal, and plastic.

21. The method of claim 18 wherein said puncturing member is in the shape of a pyramid or wedge.

22. The method of claim 21 wherein said pyramid or wedge comprises sharp edges having corner radii of less than 1 µm.

23. The method of claim 18 wherein said puncturing member is configured for puncturing said skin or mucosa to a depth of about 30–50 µm.

24. The method of claim 18 wherein said plurality of puncturing members occupy up to about 50% of the surface area of the lower surface of the base.

25. The method of claim 18 wherein said puncturing member has a dimension at a base thereof of about 10–50 µm.

26. The method of claim 18 wherein said each of said holes is positioned adjacent to a puncturing member.

27. The method of claim 18 wherein said network of channels further comprises a reservoir for holding liquid.

28. The method of claim 18 wherein said base is substantially planar.

29. The method of claim 18 further comprising a mechanism for producing vibrations, said vibrations for facilitating efficient and non-traumatic penetration of the puncturing members into the skin or mucosa.

30. The method of claim 29 wherein said mechanism for producing vibrations comprises a piezo-electric transducer.

31. The method of claim 29 wherein said mechanism for producing vibrations produces vibrations in the range of about 2000 Hz to about 100 MHz.

32. The method of claim 18 further comprising an external reservoir for holding a liquid drug composition to be delivered to the body.

33. The method of claim 32 further comprising a mechanism for limiting the rate of drug delivery, said mechanism positioned between the external reservoir and the puncturing members.

34. The method of claim 18 wherein said device is disposable.

35. A method of transdermal or transmucosal monitoring of a selected analyte in a body comprising:
   (a) providing a device comprising:
      a base having a lower side and an upper side;
      a plurality of puncturing members extending from the lower side of the base, said puncturing members configured for puncturing said skin or mucosa to a depth sufficient to reduce the barrier properties thereof without significantly damaging underlying tissues;
      a plurality of holes extending from the lower side of the base to the upper side of the base, said holes configured for permitting a liquid to move therethrough by capillary action; and
      a network of channels configured in the upper side of said base to interconnect said holes, said network of channels including a reservoir;
   (b) contacting said device with the skin or mucosa such that said plurality of puncturing members puncture the skin or mucosa to a depth sufficient to reduce the barrier properties thereof resulting in seepage of interstitial fluid to the surface of said skin or mucosa such that interstitial fluid moves by capillary action through the holes, through the channels, to the reservoir;
   (c) collecting the interstitial fluid from the reservoir; and
   (d) analyzing the interstitial fluid with respect to the selected analyte.

36. The method of claim 35 further comprising applying suction to increase the rate of collection of interstitial fluid.

37. The method of claim 35 further comprising applying ultrasonic vibrations to the skin or mucosa to increase the rate of collection of the selected analyte.

38. The method of claim 37 wherein said ultrasonic vibrations are modulated in frequency, intensity, phase, or a combination thereof.

39. The method of claim 38 wherein said ultrasonic vibrations are in the range of about 2000 Hz to about 100 MHz.

40. The method of claim 35 wherein movement of interstitial fluid by capillary action is enhanced by applying ultrasonic vibrations.

41. The method of claim 35 wherein said selected analyte is glucose.

42. The method of claim 35 further comprising applying an anticoagulant to inhibit obstruction of the holes or channels.

43. A method of transdermally or transmucosally delivering a drug in liquid form to a body comprising:
   (a) providing a device comprising:
      a base having a lower side and an upper side;
      a plurality of puncturing members extending from the lower side of the base, said puncturing members configured for puncturing said skin or mucosa to a depth sufficient to reduce the barrier properties thereof without significantly damaging underlying tissues;
      a plurality of holes extending from the lower side of the base to the upper side of the base, said holes configured for permitting a liquid to move therethrough by capillary action; and
      a network of channels configured in the upper side of said base to interconnect said holes, said network of channels including a reservoir;
   (b) contacting said device with the skin or mucosa such that said plurality of puncturing members puncture the skin or mucosa to a depth sufficient to reduce the barrier properties thereof;
   (c) supplying the drug to said reservoir such that said drug moves from the reservoir, through the channels and holes to the site of the punctures of the skin or mucosa and thus into the body.

44. The method of claim 43 further comprising applying pressure to increase the rate of delivery of the drug to the body.

45. The method of claim 43 further comprising applying ultrasonic vibrations to the skin or mucosa to increase the rate of delivery of the drug to the body.

46. The method of claim 45 wherein said ultrasonic vibrations are modulated in frequency, intensity, phase, or a combination thereof.

47. The method of claim 45 wherein said ultrasonic vibrations are in the range of about 2000 Hz to about 100 MHz.

48. The method of claim 43 wherein said drug in liquid form further comprises an anti-irritant, antiseptic, or analgesic to reduce trauma to the body due to the application of the device.

* * * * *